(12) United States Patent
Miyata et al.

(10) Patent No.: US 8,969,274 B2
(45) Date of Patent: Mar. 3, 2015

(54) SCRUB SOAP AND METHOD FOR MANUFACTURING THE SAME

(75) Inventors: Kiyoshi Miyata, Tokyo (JP); Mitsuharu Miyanohara, Aira (JP); Hidemi Kakihara, Chikushino (JP)

(73) Assignees: Chojyu-No-Sato Co., Ltd., Kanagawa (JP); Zenshin Co., Ltd., Fukuoka (JP); Ing Co., Ltd., Kagoshima (JP)

( * ) Notice: Subject to any disclaimer, the term of this patent is extended or adjusted under 35 U.S.C. 154(b) by 0 days.

(21) Appl. No.: 14/128,845

(22) PCT Filed: Jul. 7, 2011

(86) PCT No.: PCT/JP2011/065553

§ 371 (c)(1),
(2), (4) Date: Dec. 23, 2013

(87) PCT Pub. No.: WO2013/005327

PCT Pub. Date: Jan. 10, 2013

(65) Prior Publication Data

US 2014/0128306 A1    May 8, 2014

(51) Int. Cl.
*A61K 8/02* (2006.01)
*A61Q 19/10* (2006.01)
*C11D 9/20* (2006.01)
*C11D 13/10* (2006.01)
*A61K 8/36* (2006.01)

(52) U.S. Cl.
CPC ............... *A61K 8/0279* (2013.01); *C11D 9/20* (2013.01); *C11D 13/10* (2013.01); *A61K 8/361* (2013.01); *A61Q 19/10* (2013.01); *A61K 2800/28* (2013.01); *A61K 2800/412* (2013.01)
USPC ...................................................... 510/139

(58) Field of Classification Search
USPC ...................................................... 510/139
See application file for complete search history.

(56) References Cited

U.S. PATENT DOCUMENTS

| | | |
|---|---|---|
| 3,893,928 A | 7/1975 | Ono et al. |
| 4,016,229 A | 4/1977 | Tobin |
| 4,038,089 A | 7/1977 | Kawai |
| 4,839,080 A * | 6/1989 | Jungermann et al. ......... 510/131 |
| 5,017,523 A * | 5/1991 | Kimura et al. .................. 501/85 |
| 5,340,514 A * | 8/1994 | Taniguchi et al. ............ 264/434 |
| 5,661,119 A * | 8/1997 | Hersh et al. ................... 510/139 |
| 2004/0022818 A1 * | 2/2004 | Cho et al. ...................... 424/401 |

FOREIGN PATENT DOCUMENTS

| | | |
|---|---|---|
| EP | 1935957 | 6/2008 |
| JP | 2008-111015 | 5/2008 |
| JP | 2008-189703 | 8/2008 |
| JP | 2008189703 A * | 8/2008 |
| JP | 2008-239792 | 10/2008 |
| JP | 2010-90395 | 4/2010 |
| WO | WO 2007/043343 | 4/2007 |
| WO | WO2013/005327 | 1/2013 |

OTHER PUBLICATIONS

Volcanic ash-Shirasu in skin care (Kingo), 1994.*
International Search Report, PCT Appln. Serial No. PCT/JP2011/065553 mailed Sep. 20, 2011, 3 pages—Japanese; 2 pages—English.
International PCT Written Opinion of PCT Appln. Serial No. PCT/JP2011/065553—English 3 pages, Certification of English Translation 1 page.
Tomohiro Ifuku et al., "Shirasu Microballoon o Gan'yu suru Senganryo ni Kansuru Kisoteki Seizo Gijutsu", Dai 42 Kai Preprints of Joint Chemical Conference of Kyushu Branch, Jul. 2, 2005, p. 262.

* cited by examiner

*Primary Examiner* — Nicole M Buie-Hatcher
*Assistant Examiner* — M. Reza Asdjodi
(74) *Attorney, Agent, or Firm* — Andrew F. Young, Esq.; Lackenbach Siegel, LLP

(57) ABSTRACT

The present invention relates to provide a scrub soap and a method for manufacturing the same. A method for manufacturing a scrub soap includes preparing a scrub agent consisting of a shirasu and a hollow shirasu having a different average particle diameter each other, preparing a fatty acid composition consisting of at least one kind of fatty acid, preparing an alkali aqueous solution by dissolving at least one kind of alkali metal hydroxide of which molar ratio to at least one kind of fatty acid is not more than 1, and preparing a soap basis material by mixing the scrub agent, the alkali aqueous solution and the fatty acid composition.

10 Claims, 1 Drawing Sheet

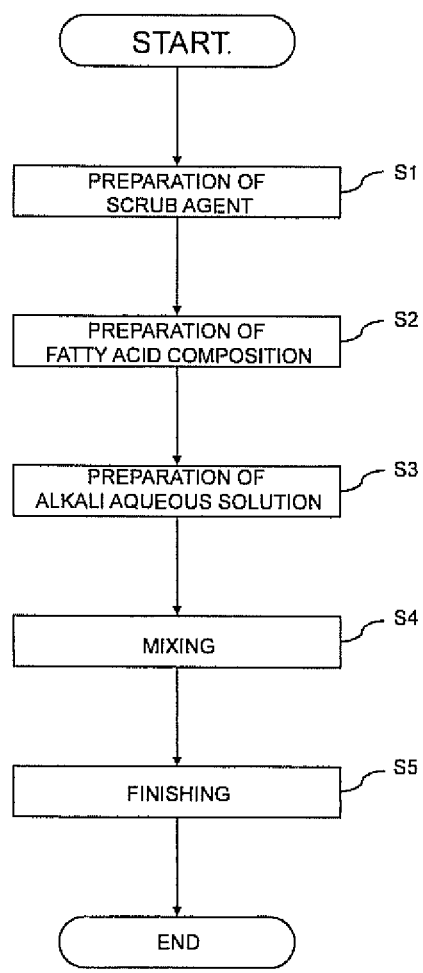

SCRUB SOAP AND METHOD FOR MANUFACTURING THE SAME

CROSS REFERENCE TO RELATED APPLICATIONS

This application claims priority to International Ser. No. PCT/JP2011/065553 filed Jul. 7, 2011, the entire contents of which are incorporated herein fully by reference.

FIGURE SELECTED FOR PUBLICATION

FIG. 1

TECHNICAL FIELD

The present invention relates to a scrub soap and a method for manufacturing the same.

BACKGROUND

Conventionally, a scrub soap combined with a scrub agent is provided to improve an effect on removal of such as dirt on the skin or old dead skin cells of the skin. The scrub agent can physically remove such as dirt on the skin or dead skin cell of the skin by rubbing and adsorbing so that cleaning effect of the soap can be increased.

A material as the scrub agent includes e.g. rice bran, azuki bean, toasted soybean flour, konjac, seaweed, corn flour, oatmeal, crystalline cellulose, apricot seeds, walnut shell particles, polyethylene, polystyrene, nylon, alumina, silica, talc, volcanic glassy sediment, and shirasu.

The pore size on the human face is average 80-150 μm and if the particle size of the scrub agent combined with the soap is smaller than the pore, such as pore clogging dirt or dead skin cells can be efficiently removed.

Further, it is ideal to provide a scrub soap having high cleaning and scrubbing effect despite a small amount in use, in which a combined amount of the scrub agent is as large as possible. If the amount used is suppressed, the environment load can be decreased.

On the other hand, the larger amount of the scrub agent is combined the more likely the separation between the scrub agent and the liquid component occurs during manufacturing, and it is difficult to make the product keeping the homogeneous mixed state of materials because the scrub agent precipitates.

Further, it is problematic that when the large amount of the scrub agent, which is fine powder, are combined, the mechanical mixing becomes impossible and productivity thereof extremely decrease because viscosity of the mixture of materials extremely increases and fluidity thereof decreases.

In Patent Document 1, a method for manufacturing a scrub soap is disclosed, in which a large amount of scrub agents is combined. While, medium chain fatty acid esters or ethyl alcohol as a fluidization auxiliary agent is added in separate to increase fluidity of materials. Accordingly, because the number of materials used increases, an adjustment of the combination amount of materials becomes complicated and the number of steps of manufacturing process consequently increases. In addition, it is problematic that affinity of medium chain fatty acid esters for a soap is bad and the soap likely separates therefrom. Further, while a means to increase fluidity of materials is disclosed in Patent Document 1, no means to solve the precipitation problem of the scrub agent resulting from separation between the scrub agent and the liquid component is disclosed.

Further, a volcanic glassy sediment represented by shirasu as a raw material for a scrub agent is noticeable because of high cleaning effect thereof. In Patent Document 2, the inventor of the present invention proposed the method to manufacture a scrub soap combined with a shirasu balloon as the scrub agent thereof, which is obtained by quellung processing of shirasu. A scrub soap manufactured by using such method has a property of which the soap component of the soap formed inside of the hollow shirasu balloon is gradually eluted therefrom in use and accordingly bubbling is characteristically long-lasting.

However, in contrast to improved long-lasting bubbling due to forming the soap inside the shirasu balloon, it is problematic that lathering (foaming at the beginning of the use of the scrub soap) is sacrificed.

Then, when the shirasu balloon and the shirasu with no hollow were mixed to make a scrub agent to provide both long-lasting bubbling and good lathering, viscosity on manufacturing becomes very high so that mechanical mixing and homogeneous dispersion of the scrub agent become difficult issues despite the same combination amount used as before.

PRIOR ART

Patent Document

Patent Document: Laid Open JP 2008-239792
Patent Document: Laid Open JP 2008-189703

SUMMARY OF THE INVENTION

Objects to be Solved

The purpose of the present invention is to provide an efficient manufacturing method for a scrub soap containing a large amount of volcanic glassy sediments represented especially by the shirasu as a scrub agent made of a water insoluble fine particle powder and providing both long-lasing bubbling and better lathering without compromising and without using only fluidization auxiliary agent.

The purpose of the present invention is to provide a scrub soap containing a large amount of volcanic glassy sediments represented especially by the shirasu as a scrub agent made of a water insoluble fine particle powder and providing both long-lasing bubbling and better lathering without compromising.

Means to Solve the Objects (1) A manufacturing method for a scrub soap comprises; a step of preparing a scrub agent consisting of the shirasu and the hollow shirasu having a different average particle diameter each other, a step of preparing a fatty acid composition consisting of at least one kind of fatty acid, a step of preparing an alkali aqueous solution by dissolving at least one kind of alkali metal hydroxide of which molar ratio to at least one kind of fatty acid is not more than 1, and a step of preparing a soap basis material by mixing the scrub agent, the alkali aqueous solution and the fatty acid composition.

(2) Further, in the step of preparing the soap basis material, at least 10% by weight of the scrub agent relative to the total weight of the soap basis material is combined in the above manufacturing method for a scrub soap.

(3) Further, in the manufacturing method for a scrub soap, an average particle diameter of the shirasu is in the range of 2-10 μm.

(4) Further, in the manufacturing method for a scrub soap, an average particle diameter of the hollow shirasu is in the range of 30-50 μm.

(5) Further, in the manufacturing method for a scrub soap, the scrub agent contains at least 70% by weight of the shirasu.

(6) In addition, the scrub soap contains the shirasu and the hollow shirasu having a different average particle diameter each other.

(7) Further, the scrub soap contains at least 10% by weight of the scrub agent.

(8) Further, an average particle diameter of the shirasu of the scrub soap is in the range of 2-10 μm.

(9) Further, an average particle diameter of the hollow shirasu of the scrub soap is in the range of 30-50 μm.

(10) Further, the scrub agent of the scrub soap contains at least 70% by weight of the shirasu.

Effects of the Invention

According to the present invention, a scrub soap containing a large amount of volcanic glassy sediments represented especially by the shirasu as a scrub agent made of a water insoluble fine particle powder and providing both long-lasing bubbling and better lathering without compromising and without using any fluidization auxiliary agent can be manufactured efficiently.

According to the present invention, a scrub soap containing a large amount of volcanic glassy sediments represented especially by the shirasu as a scrub agent made of a water insoluble fine particle powder can provide both long-lasing bubbling and better lathering without compromising.

BRIEF DESCRIPTION OF THE DRAWINGS

FIG. 1 illustrates a manufacturing process of a scrub soap according to the present invention.

EXAMPLE

Referring to FIGURE, the inventor further illustrates specific Example of the present invention.

Meantime, according to the present invention, the average particle diameter is the particle diameter at 50% integration value of the particle distribution obtained by using a laser diffraction/scattering particle distribution measurement apparatus 1. [Preparation Process of Each Material]

The inventor illustrates a preparation method for a scrub agent, an alkali aqueous solution and a fatty acid composition used in the present Example.

1-1. [Preparation Process of a Scrub Agent (S1)]

According to the present Example, inorganic compounds including volcanic glassy sediment such as shirasu, silicic acid, silicate, aluminum silicate and aluminum oxide as a raw material for a scrub agent can be used. Preferably, volcanic glassy sediment, especially shirasu, can be used. Further, more than two kinds of the scrub raw materials can be used. Hereinafter, the inventor illustrates Example of the present invention, wherein the shirasu is used as a raw material of a scrub material.

The shirasu first is ground to provide particles having 3-5 μm average diameter by such as a vibrational mill.

Then, after the obtained shirasu having 3-5 μm average particle diameter is dried for 3 hours at 200° C., the shirasu is burned in a fluidized combustion furnace at 900-1200° C., preferably at 950-1050° C. The shirasu results in foaming and being hollow powder (shirasu balloon.)

The obtained hollow powder is screened by 200 mesh screen to provide the shirasu having 30-50 μm average particle diameter excluding the powder larger than 75 μm. The average particle diameter of the hollow shirasu of the scrub agent is 30-50 μm so that the scrub soap can have long-lasting bubbling. Meantime, the powder larger than 75 μm is excluded to improve safety on an eye when the scrub soap is used. The powder that is smaller than 75 μm hurts an eye less likely.

Further, the hollow powder (shirasu balloon) obtained by the above process is ground to provide particles having 2-10 μm average particle diameter by such as a vibrational mill, differently from the hollow shirasu having 30-50 μm average particle diameter.

Both the hollow shirasu having 30-50 μm average particle diameter and the shirasu having 2-10 μm average particle diameter, which are burned and water-insoluble inorganic fine particle powder, can be used adequately as a scrub agent in the manufacturing process for the scrub soap as described later. Further, each can be used independently or in mixing as a scrub agent.

The scrub soap combined with the hollow shirasu having 30-50 μm average particle diameter is characterized by providing a long-lasting bubbling.

On the other hand, the shirasu having 2-10 μm average particle diameter is characterized by a good affinity for the skin and high dirt-adsorbing property. The contact area with pore dirt on the skin becomes large by making the scrub particle fine particle so that the dirt can be assuredly removed by adsorbing. The reason why the shirasu having particle diameter larger than 2 μm is used is that the particle having diameter larger than that provides scrub feeling. Further, from affinity for the skin standpoints, the particle diameter is preferably smaller than 10 μm and such shirasu less likely damages the skin. Further, by combining such fine scrub agent, foam generated on cleaning is fine so that the sense of use of the soap may be good.

Accordingly, by mixing the predetermined amount of the shirasu having 2-10 μm average particle diameter and the hollow shirasu having 30-50 μm average particle diameter, a mixed shirasu consisting of two shirasu particle groups having different average particle diameter is made and combined as a scrub agent so that a scrub soap having the above advantages from two kinds of shirasu can be provided.

In such case, it is preferable that a combined amount of the hollow shirasu having 30-50 μm average particle diameter in the mixed shirasu is less than 30% by weight, i.e. a combined amount of the shirasu having 2-10 μm average particle diameter in the mixed shirasu is more than 70% by weight. If the combined amount of the shirasu having 2-10 μm average particle diameter in the mixed shirasu is more than 70% by weight, agitation of material mixture in the preparation process of the soap basis material becomes efficient by a machine so that dispersion of the shirasu can occur homogeneously and easily. If the combined amount of the hollow shirasu in the shirasu mixture is over than 30% by weight, the material mixtures becomes harder. This is likely due to high water absorbency of the hollow shirasu.

1-2. [Preparation Process of a Fatty Acid Composition (S2)]

According to the present Example, a saturated fatty acid or an unsaturated fatty acid having a carbon number of 10-20 can be used. In general, a mixture of more than two kinds of fatty acid, according to the present Example, is used as a fatty acid composition but also only one kind of fatty acid can be used.

Because the higher carbon number of a fatty acid the higher melting point thereof is, the viscosity of the soap basis material prepared in the manufacturing process of a soap increase if a fatty acid having high carbon number is used relatively more. Further, as to the properties of the manufactured soap, when a high carbon number of the fatty acid is used relatively more, cleaning power thereof increases and the bubbling is longer-lasting but lathering thereof inclines to decrease. In addition, as to skin irritation, the lower carbon number of a fatty acid is used the stronger irritation occurs.

As results from keen examination, considering comprehensively the viscosity of the soap basis material and the properties of the soap, it is clearly preferable that each content of the fatty acids of the fatty acid composition is 4-5% by weight of lauric acid, 62-72% by weight of myristic acid, 10-14% by weight of palmitic acid and 14-18% by weight of stearic acid and the total content of lauric acid, myristic acid, palmitic acid and stearic acid is more than 99% by weight relative to the total weight of the fatty acid composition.

1-3. [Preparation Process of an Alkali Aqueous Solution (S3)]

According to the present Example, potassium hydroxide and sodium hydroxide can be used as an alkali metal hydroxide. Further, a mixture of potassium hydroxide and sodium hydroxide can be used as well.

First, water is added to a tank such as a compounding container that can be heated and vacuumed, and then an alkali metal hydroxide is gradually added to prepare 3.5-4.7 mol/L alkali aqueous solution. If the concentration of the alkali aqueous solution is in the above range, no drying process is needed in the preparation process of a scrub soap as described later and in addition, the viscosity of the material mixture in the preparation process of the soap basis material can be maintained adequately. As results, the scrub soap can be manufactured more efficiently. In the case of the concentration of the alkali aqueous solution which is not higher than 3.5 mol/L, a drying process to evaporate a large amount of water is needed because the water content of the soap basis material becomes large as described later. Further, in the case of the concentration of the alkali aqueous solution which is over 4.7 mol/L, a homogeneous mixing of materials can be more difficult because the water content of the soap basis material becomes less.

Specifically, it is desirable that temperature of the solution is being kept closer to room temperature, e.g. around 15-35° C., as long as possible because temperature of the solution rises when an alkali metal hydroxide is added to water.

Further, the other component can be added to improve the property of the scrub soap within the range in which the manufacturing efficiency is not damaged in the manufacturing process of the scrub soap as described later, i.e. an extreme increase or decrease of the viscosity of the material mixture does not occur. As other components, e.g. glycerin or other humectant such as higher alcohols, foaming agents, water soluble polysaccharides and surfactants can be selected.

2. [Manufacturing Process of a Scrub Soap]

Hereinafter, the inventor illustrates the manufacturing process of the scrub soap using the scrub agent, the alkali aqueous solution and the fatty acid composition obtained by the above processes (S1-3).

2-1. [Preparation Process of a Soap Basis Material (S4)]

The hollow shirasu having 30-50 μm average particle diameter, the shirasu having 2-10 μm average particle diameter or the mixed shirasu obtained by mixing two kinds of shirasu thereof, which are prepared in the preparation process (S1) of the above scrub agent can be used as a scrub agent.

According to the present Example, the scrub agent can be added up to 30% by weight of the soap basis material being prepared. If the combination amount of the scrub agent is less than 30% by weight, the viscosity of the mixed material mixed in the preparation process of the soap basis material can be controlled around the level on which the mechanical agitation is workable so that the scrub soap can be manufactured more efficiently. Further, it is preferable that the combination amount of the scrub agent more than 10% by weight relative to the total weight of the soap basis material being prepared to make the scrub soap having satisfactory scrubbing effect.

Further, according to the present Example, the use amount of the fatty acid composition and the use amount of the alkali aqueous solution should be determined so that the soap basis material being prepared can be in an excess state of the fatty acid. Specifically, the use amounts of the fatty acid composition and the alkali aqueous solution are adjusted so that the fatty acid by mass consisting of the fatty acid composition is excessively more than the alkali metal hydroxide dissolved in the alkali aqueous solution by mass and the ratio (molar ratio) of the fatty acid by mass to the alkali metal hydroxide by mass is not more than 1.

In this manner, the material mixture in the preparation process of the soap basis material is in an excess state of the fatty acid and the unneutralized fatty acid is accordingly present so that the viscosity of the material mixture can be lowered. As results, agitation of the material mixture becomes easy so that the preparation of the soap basis material can be efficiently conducted. In addition, the unneutralized fatty acid works as a dispersant so that even if the scrub agent over 10% by weight is combined, the liquid component and the water insoluble solid component are being kept in the homogeneous mixing state without separation.

It is further preferable that the molar ratio is larger than 0.85 at least. Given this condition, the scrub soap can have an appropriate viscosity so that feeling in use may be good. If the molar ratio is not larger than 0.85, the large amount of free fatty acid is included in the scrub soap to be manufactured so that the soap is too soft and even the fatty acid thereof may cause skin irritation.

Hereinafter, the inventor illustrates a specific preparation process of a soap basis material.

First, an alkali aqueous solution is poured into the compounding container and a scrub agent is added while agitating. At this step, the scrub agent is so very fine powder that it may be likely drifted on the air while agitating in the compounding container. Therefore, the inside of the solution and the surface of the solution are agitated slowly (e.g. at around 20-40 rpm) at the beginning and then strong eddy is generated by such as a disperser to agitate and mix (e.g. at around 800-1200 rpm), as if incorporating it inside the solution in order to agitate in the compounding container, so that the scrub agent may be prevented from drifting on the air as powder dust.

In parallel, temperature of the solution is gradually elevated until 80° C. during agitation. Elevation of temperature can be carried out by an electric heater or by heating with steam.

Next, the heated fatty acid composition at 70-90° C. to melt is added to the compounding container. At this step, the agitation is carried out while degassing (defoaming) the air inside of the mixed solution by vacuuming the compounding container. As results, the fatty acid salt is generated by neutralization reaction between the alkali metal hydroxide and the fatty acid so that the preparation process for the soap basis material can be completed.

In the neutralization reaction process between the alkali metal hydroxide and the fatty acid, the mixed solution is agitated for 20 min while keeping temperature of the solution at 75-85° C. If temperature of the mixed solution is below 75° C., it is not desirable because the liquidity is lowered, the mixed solution becomes hard and the agitation efficiency drops. Further, if temperature of the mixed solution is over 85° C., the mixed solution is easily discolored, i.e. causing baked soap, and it is not desirable because the product's finishing appearance is poor. Temperature of the mixed solution is in the range of 75-85° C. and more preferably 77-83° C. so that the smooth and homogeneous and even saliently white scrub soap can be obtained.

According to the above description, after dispersion of the scrub agent in the alkali aqueous solution, the fatty acid composition is added to make the soap basis material, but according to the present invention, after dispersion of the scrub agent in the fatty acid composition, the process in which the alkali aqueous solution is added or the process in which mixing the alkali aqueous solution and the fatty acid composition and at the same time addition and dispersion of the scrub agent are conducted can be carried out appropriately to prepare the soap basis material. Meantime, if after mixing the alkali aqueous solution and the fatty acid composition, the scrub agent is added; it is not desirable that it becomes difficult to homogeneously disperse the scrub agent because of mixing the fatty acid salt generated by neutralization and the scrub agent.

Meantime, according to the present embodiment, the scrub soap is manufactured by neutralization reaction of the fatty acid, but a scrub soap can be manufactured by saponification reaction, mixing fat and an alkali aqueous solution. While, in case of saponification of fat, a large amount of glycerin generated by hydrolysis of fat must be removed by additional salting-out process to remove generated glycerin, and it is not desired because manufacturing efficiency thereof on the scrub soap decreases.

2-2. [Finishing Process (S5)]

The soap basis material prepared by the above processes can be as-is a finishing product of the scrub soap, but also component for beauty or fragrance can be added and a scrub soap having further desired properties can be provided. Further, a drying process to adjust water content can be conducted.

EXAMPLE AND COMPARATIVE EXAMPLES

Hereinafter, the inventor illustrates specific Example and Comparative Examples.

According to the present Example and Comparative Example, each combination ratios are shown in Table 1. Further, in Table 1, when all materials are mixed, the weight (weight of the soap basis material) thereof is 100% by weight.

TABLE 1

|  | Example | Comparative Example 1 | Comparative Example 2 | Comparative Example 3 |
|---|---|---|---|---|
| A. Alkali aqueous solution component | | | | |
| Purified water | 23.994 | 23.684 | 27.424 | 23.684 |
| Potassium hydroxide | 5.89 | 6.2 | 5.46 | 6.2 |
| Humectant | 12 | 12 | 12 | 12 |
| White pigment | 4 | 4 | 4 | 4 |
| Saccharides | 0.01 | 0.01 | 0.01 | 0.01 |
| Anti-inflammation agent | 0.1 | 0.1 | 0.1 | 0.1 |
| Surfactant | 7 | 7 | 7 | 7 |
| B. Scrub agent (mixed shirasu) | | | | |
| Shirasu (average particle diameter 5 μm) | 17 | 17 | 17 | 19 |
| Hollow shirasu (average particle diameter 45 μm) | 5 | 5 | 5 | 3 |
| C. Fatty acid composition | | | | |
| Lauric acid 98 | 1 | 1 | 1 | 1 |
| Myristic acid 98 | 17 | 17 | 17 | 17 |
| Palmitic acid 98 | 1 | 1 | 1 | 1 |
| Stearic acid 65 | 6 | 6 | 3 | 6 |
| D. Others | | | | |
| Component for beauty/active component composition | 0.006 | 0.006 | 0.006 | 0.006 |
| Total | 100 | 100 | 100 | 100 |

Unit: % by weight

In Table 1, Lauric acid 98, Myristic acid 98, Palmitic acid 98 and Stearic acid 65 are obtained from Miyoshi Oil & Fat Co., Ltd. Laurie acid 98 consists of 98% by weight of lauric acid, 1% by weight of capric acid and 1% by weight of myristic acid. Myristic acid 98 consists of 98% by weight of myristic acid, 1% by weight of lauric acid and 1% by weight of palmitic acid. Palmitic acid 98 consists of 98% by weight of palmitic acid, 1% by weight of myristic acid and 1% by weight of stearic acid. Stearic acid 65 consists of 66% by weight of stearic acid, 32% by weight of palmitic acid, 1% by weight of myristic acid and 1% by weight of arachidic acid.

Further, the composition of other components for beauty and active components were added in the finishing process (S5).

The combination ratio of Example in Table 1, the ratio (molar ratio) between fatty acid by mass and potassium hydroxide by mass is 0.95. As to the combination ratio of each shirasu of the scrub agent (mixed shirasu), 77.3% by weight of the shirasu having 5 μm average particle diameter and 22.7% by weight of the hollow shirasu having 45 μm average particle diameter are combined. Each component ratio of each fatty acid of the fatty acid composition calculated based on the purity of each fatty acid is 4.6% by weight for lauric acid, 67% by weight for myristic acid, 12.3% by weight for palmitic acid and 15.9% by weight for stearic acid, and 99.8% by weight of these four fatty acids relative to the total weight of the fatty acid composition.

As for the combination ratio in Comparative Example 1, the molar ratio between the fatty acid and potassium hydroxide is 1.05, and others are the same as above Examples.

As for the combination ratio in Comparative Example 2, the molar ratio between the fatty acid and potassium hydroxide is 1.06. Each component ratio of each fatty acid of the fatty acid composition is 5.23% by weight for lauric acid, 76% by weight for myristic acid, 9.59% by weight for palmitic acid and 9.05% by weight for stearic acid, and 99.87% by weight of these four fatty acids relative to the total weight of the fatty acid composition. Others are the same as the above Example. The purpose to select this combination ratio is to examine if the mechanical agitation and homogeneous mixing is workable or not under non-excess fatty acid condition when the viscosity of the mixed material decreases by reducing the amount of stearic acid that has 18 carbon atoms and a large molecular weight.

As for the combination ratio in Comparative Example 3, the molar ratio between the fatty acid and potassium hydroxide is 1.05. As for the combination ratio of each shirasu of the scrub agent (mixed shirasu), 86.4% by weight of the shirasu having 5 μm average particle diameter and 13.6% by weight of the hollow shirasu having 45 μm average particle diameter are combined, and others are the same as the above Example.

Among these Example and Comparative Examples, the scrub soap was only able to be actually manufactured by using the combination ratio of Example. In the case of Comparative Examples, no preferable soap basis material was prepared due to increasing of viscosity of the mixed material.

Further, the scrub soap manufactured using the combination ratio of Example provided homogeneously dispersed scrub agent. Further, when in use, all results including lathering, long-lasting bubbling, and cleaning power were good.

Further, the above described Example is one of Examples of the present invention and the present invention is not limited to the scope of Example. Accordingly, even if out of the above Example, a variety of changes corresponding to such as design can be made without departing from the technical aspect of the present invention.

For Example, the combination ratio of each material disclosed in the present invention is one of Examples of the present invention, any scrub soap can be made appropriately without departing from the scope described in the above Example, and a soap having good properties in all aspects including lathering, long-lasing bubbling and cleaning power can be made,

What is claimed is:

1. A method for manufacturing a scrub soap, comprising the steps of:
    preparing a scrub agent consisting of a hollow shirasu component and a ground hollow shirasu component, each respective component having a different average particle diameter from the other,
    preparing a fatty acid composition consisting of at least one kind of fatty acid,
    preparing an alkali aqueous solution by dissolving at least one kind of alkali metal hydroxide, and
    preparing a soap basis material by mixing the scrub agent, the alkali aqueous solution and the fatty acid composition, wherein the molar ratio of said alkali metal hydroxide to said fatty acid is greater than 0.85 and not more than 1, thereby forming the scrub soap.

2. The method for manufacturing the scrub soap according to claim 1, characterized by the step of combining at least 10% by weight of said scrub agent relative to a total weight of said soap basis material.

3. The method for manufacturing the scrub soap according to claim 1, wherein the average particle diameter of said ground hollow shirasu component is 2-10 μm.

4. The method for manufacturing the scrub soap according to claim 1, wherein the average particle diameter of said hollow shirasu component is 30-50 μm.

5. The method for manufacturing the scrub soap according to claim 1, wherein said scrub agent contains at least 70% by weight of said ground hollow shirasu component.

6. A scrub soap comprising:
    a scrub agent consisting of a ground hollow shirasu component and a hollow shirasu component, each having a different average particle diameter from the other.

7. The scrub soap according to claim 6, wherein said scrub soap comprises at least 10% by weight of said scrub agent.

8. The scrub soap according to claim 7, wherein the average particle diameter of said ground hollow shirasu component is 2-10 μm.

9. The scrub soap according to claim 8, wherein the average particle diameter of said hollow shirasu component is 30-50 μm.

10. The scrub soap according to claim 9, wherein said scrub agent contains at least 70% by weight of said ground hollow shirasu component.

* * * * *